United States Patent
Hollebone et al.

(10) Patent No.: US 7,727,772 B2
(45) Date of Patent: Jun. 1, 2010

(54) FLUID CONTAMINATION ANALYZER AND A SAMPLE CELL THEREFOR

(75) Inventors: Bryan R. Hollebone, Ottawa (CA); John Wendell Dawson, Ottawa (CA); Rajesh Krishnamurthy, Kanata (CA); Michael Allan Donkers, Ottawa (CA)

(73) Assignee: Ecovu Analytics Inc., Ottawa, Ontario (CA)

( * ) Notice: Subject to any disclaimer, the term of this patent is extended or adjusted under 35 U.S.C. 154(b) by 470 days.

(21) Appl. No.: 11/435,720

(22) Filed: May 18, 2006

(65) Prior Publication Data

US 2006/0263896 A1    Nov. 23, 2006

Related U.S. Application Data

(60) Provisional application No. 60/681,714, filed on May 18, 2005.

(51) Int. Cl.
  *G01N 21/03*  (2006.01)
  *G01N 21/00*  (2006.01)
  *G01N 1/18*   (2006.01)
  *G01N 35/08*  (2006.01)

(52) U.S. Cl. .................. 436/165; 436/177; 436/164; 436/55; 422/82.05

(58) Field of Classification Search .............. 436/55, 436/165, 177, 164
See application file for complete search history.

(56) References Cited

U.S. PATENT DOCUMENTS

| 3,946,239 | A | | 3/1976 | Salzman |
|---|---|---|---|---|
| 4,076,420 | A | * | 2/1978 | De Maeyer et al. ........... 356/73 |
| 4,188,543 | A | | 2/1980 | Brunsting |
| 4,200,802 | A | | 4/1980 | Salzman |
| 4,245,910 | A | | 1/1981 | Kallander |

(Continued)

FOREIGN PATENT DOCUMENTS

CA    2504703 A1 * 10/1994

(Continued)

OTHER PUBLICATIONS

A. Yu. Andryushchenko*, A.B. Blank, S.V. Budakovsky, N.Z. Galunov, N.I. Shevtsov, O.A. Tarasenko. "Scintillation material for determination of radionuclides in water," Nuclear Instruments and Methods in Physics Research A 511 (2003) 425-430.*

(Continued)

*Primary Examiner*—Sam P Siefke
*Assistant Examiner*—Bryan T Kilpatrick
(74) *Attorney, Agent, or Firm*—Victoria Donnelly; IP-Mex Inc.

(57) ABSTRACT

A fluid contamination analyzer has a sample cell containing a trapping medium capable of trapping contaminants suspended in the aqueous fluid flowing through the trapping medium, a light source for illuminating the trapping medium to cause the entrapped contaminants generate a secondary radiation indicative of the identity and quantity of the contaminants, and a photodetector for receiving the secondary radiation. The fluid contamination analyzer has a reflective shell in the form of an ellipsoid extending at least partially around the sample cell and the detector, the sample cell being positioned at one of the focal points of the ellipsoid, and the photodetector at the other point of the ellipsoid to receive the secondary radiation reflected by the reflective shell.

34 Claims, 4 Drawing Sheets

U.S. PATENT DOCUMENTS

| | | | | |
|---|---|---|---|---|
| 4,304,996 | A | * | 12/1981 | Blades .................... 250/373 |
| 4,557,603 | A | | 12/1985 | Oehler |
| 4,808,825 | A | | 2/1989 | Miyatake |
| 4,861,163 | A | | 8/1989 | Bach |
| 5,512,491 | A | | 4/1996 | Mehkeri |
| 6,563,137 | B2 | * | 5/2003 | Uchida ....................... 257/84 |
| 6,723,554 | B1 | * | 4/2004 | Gaillon et al. ........... 435/288.7 |

FOREIGN PATENT DOCUMENTS

| | | |
|---|---|---|
| WO | WO 9424553 A2 * | 10/1994 |

OTHER PUBLICATIONS

John Pickering et al. "Double-integraing-shpere system for measuring the optical properties of tissue", Applied Optics, Feb. 1, 1993, vol. 32., No. 4, p. 399-410.

Goran Gustafsson "Experiments on shock-wave focusing in an elliptical cavity", J. Appl. Phys., 61 (11), Jun. 1, 1987.

Directed Light Inc. of San Jose, California USA "Cavities" at http://www.directedlight.com/components/cavities.html, Copiright 2004.

Ball Seminconductor Inc. of Allen, Texas, USA at http://www.ballsemi.com/NEW/BallTech/Wspherical/Wspherical.asp, prior to May 18, 2005.

* cited by examiner

FLUID CONTAMINATION ANALYZER AND A SAMPLE CELL THEREFOR

RELATED APPLICATIONS

This application claims benefit of U.S. Provisional Patent Application to Hollebone et al, Ser. No. 60/681,714 filed on 18 May 2005, which is incorporated herein by reference.

FIELD OF THE INVENTION

This invention relates to fluid contamination analyzers, and more specifically, to an apparatus and method, which perform a dual function of entrapping contaminants present in the aqueous fluid to be analyzed, and analyzing the identity and concentration thereof by using optical methods.

BACKGROUND OF THE INVENTION

It is known that water may contain impurities and contaminants, either soluble or non-soluble, e.g. in suspension, that may be harmful to human health even if present at ultra-trace levels. This concern has already given rise to numerous methods and systems of trace level water analysis. The contaminants, which are also called "analytes", in the context of trace contaminant analysis media, apparatus and procedures, e.g. heavy metals, certain organic compounds, organic microorganisms, may be present at levels of parts per billion (ppb) or trillion (ppt), or less.

In the U.S. Pat. No. 5,512,491, a trapping medium of a microporous absorbent material is described, which provides entrapping of colloidal and other suspended matter present in water flowing through the medium. After a sufficient amount of the suspended matter has been entrapped in the medium, ultra-trace analysis of the entrapped analytes is carried out either by optical methods (photometry, fluoroscopy, spectroscopy or other) or by extraction.

Optical methods are usually more efficient and accurate for the trace analysis purposes. They typically require a source of excitation light for illuminating a sample containing analytes, causing it to emit a secondary light signal, e.g. transmitted, reflected, fluorescent, luminescent, scattered light or other, indicative of the presence and amount of analytes in the sample, and a detector for receiving the secondary light signal and interpreting it as a measure of fluid contamination.

Typically, the intensity of the secondary light signal is very low, as explained e.g. in the U.S. Pat. No. 4,245,910 (Kallander), where a scattered secondary light has been measured, which also varies strongly in various directions. Typically, samples containing analytes are unoriented emitters, which emit secondary light in the full $4\pi$ steradian angle. In addition, the level of the secondary light may be as low as individual photon count.

It is thus advisable to collect as much as possible of the secondary light signal at the detector to obtain a reliable contamination reading.

Such means have been known in the art. In early days, it has been suggested to use an integrating sphere for an improved light collection. However, it presents two practical problems, first, the optimum emission and detection foci are coincident at the centre of the integrating sphere, meaning the two optical intensities could not be discriminated. Secondly, the optimum positions of sample and detector are likewise coincidental. Thus, the mechanical requirements of locating these components are mutually exclusive.

In practice, one of the two optical functions of emitting or detecting light can be removed to the outside, being replaced, e.g. by a beam entering or exiting through a small opening in the integrating sphere. However, this immediately means that the sphere is degraded to a monofunctional optical component, rather than serving as a complete optical system. A description of single and double integrating spheres is provided, e.g. in the article by John W. Pickering, Scott A. Prahl, Niek van Wieringen, Johan F. Beek, Henricus J. C. M. Sterenborg, and Martin J. C. van Gemert, "Double-integrating-sphere system for measuring the optical properties of tissue", APPLIED OPTICS, Vol. 32, No. 4, 1 Feb. (1993).

Other examples of efficient collection of light are described in the above mentioned U.S. Pat. No. 4,245,910, and also U.S. Pat. No. 4,188,543 issued to Brunsting et al.; U.S. Pat. No. 4,808,825 to Miyatake et al.; U.S. Pat. Nos. 4,200,802 and 3,946,239 to Salzman et al.; U.S. Pat. No. 4,861,163 to Bach; and U.S. Pat. No. 4,577,603 to Oehler et al. These references describe various types of reflective shells of an ellipsoidal or semi-ellipsoidal shape, which have two foci spaced from each other, and where the sample is disposed at one focal point, while the detector is placed at the other focal point to collect the secondary light emitted by the sample and reflected by the shell.

Certain other prior art applications using elliptical geometry include shock wave experiments, which focus an emission from one focus onto another focus, thereby creating a compressed liquid jet, see Gustafsson G., "Experiments on Shock-wave Focusing in an Elliptical Cavity", J. Appl. Phys. 61, 1 Jun. (1987), and elliptical flash lamp setups for pumping solid state lasers, where the two-dimensional ellipsoidal geometry is used to deliver as much of the excitation energy to the lasing media as possible, see e.g. various laser cavity products manufactured by Directed Light Inc. in San Jose, Calif., USA as described in detail at http://www.directedlight.com/components/cavities.html(© 2004). It is therefore necessary to provide effective entrapping of contaminants present in the fluid to be analyzed, effective illumination of the entrapped contaminants to generate the secondary light of sufficient intensity, and to provide effective collection of the secondary light on the detector to ensure reliable measurements of the fluid contamination level.

In spite of the certain progress being made in the field of fluid contamination analysis, the need still exists in the industry for developing an improved apparatus for analyzing contaminants suspended in water or other fluids, which would be compact, portable, multi-functional, and have sufficient sensitivity for measuring trace amounts of contaminants.

SUMMARY OF THE INVENTION

It is therefore an object of the present invention to provide an improved fluid contamination analyzer and a sample cell therefor.

According to one aspect of the invention, there is provided a fluid contamination analyzer comprising:

(a) a sample cell, comprising:
  (i) a trapping medium for entrapping a contaminant from an aqueous fluid flowing through the trapping medium; and
  (ii) a radiation source illuminating the trapping medium with excitation radiation to cause the entrapped contaminant to generate a secondary radiation indicative of the identity, or the identity and concentration, of the contaminant;

(b) a detector for detecting the secondary radiation; and (c) a reflective shell at least partly encompassing the sample cell and the detector, the shell having a shape defining two focal points so that radiation generated at one of the focal points is substantially reflected by the reflective shell to the other focal point, the sample cell being disposed at or in close proximity to one of the focal points, and the detector being disposed at or in close proximity to the other focal point to receive the secondary radiation generated by the entrapped contaminant.

Conveniently, the radiation source is illuminating the trapping medium and the detector is detecting the secondary radiation at the same time as the fluid is flowing through the trapping medium. Alternatively, these functions can be performed sequentially.

Preferably, the reflective shell has a shape of ellipsoid, or a truncated ellipsoid.

Alternatively, the reflective shell may have one of the following shapes: a hyperboliod; a truncated hyperboliod; a paraboloid; a truncated paraboloid.

Preferably, the secondary radiation is a fluorescent radiation generated by the entrapped contaminant. Alternatively, the secondary radiation may be one of the following: Magnetic Circular Dichroism (MCD) radiation; Scattering radiation, e.g. Raman scattering radiation; Scintillation radiation; Photo-Acoustic radiation; Fluorescence radiation; Phosphorescence radiation, Luminescence radiation or other. Yet alternatively, the excitation radiation illuminating the trapping medium may be partially or completely absorbed by the entrapped contaminants. In this case a transmittance radiation passing through the trapping medium that has not been absorbed by the entrapped contaminants will be considered as a secondary radiation indicative of the presence of contaminants.

In the embodiment of the invention, the detector comprises two back-to-back photo-detectors, having their detecting windows facing in substantially opposite directions. Alternatively, the detector may comprise a semiconductor ball, which is used as a detecting component in the detector.

In the fluid contamination analyzer of the embodiment of the invention, the trapping medium is translucent, and the light source is disposed to illuminate the trapping medium from inside thereof outwards.

Conveniently, the trapping medium has an essentially closed form with a cavity formed inside thereof, and the radiation source is placed inside the cavity.

Preferably, the sample cell has a substantially spherical shape, and the trapping medium comprises a concentric layer of the trapping medium.

The radiation source comprises a light source generating excitation light at the excitation line of the contaminant of interest, and a diffuser for dispersing the excitation light substantially in a $4\pi$ steradian angle.

The sample cell has a fluid inlet communicating with the trapping medium, and a fluid outlet for discharging the fluid that has passed through the trapping medium.

Additionally, the sample cell comprises an outer transparent shell, which blocks radiation from the radiation source and passes through the secondary radiation. The outer transparent shell may further incorporate a scintillation material for detecting radioactive elements in the fluid to be analyzed. As an alternative, the trapping medium is translucent and has a shape resembling a disk or a slab, having a side surface and respective top and bottom surfaces, the radiation source being disposed to illuminate the trapping medium through the side surface, or alternatively through at least one of the top or bottom surfaces, causing the contaminant to generate the secondary light through at least one of the top and bottom surfaces.

According to another aspect of the invention, there is provided a sample cell, comprising:
a trapping medium for entrapping a contaminant from an aqueous fluid flowing through the trapping medium; and
a radiation source illuminating the trapping medium with excitation radiation to cause the entrapped contaminant to generate a secondary radiation indicative of the identity, or both the identity and concentration, of the contaminant.

Conveniently, the radiation source is illuminating the trapping medium at the same time as the aqueous fluid is flowing through the trapping medium. Alternatively, these steps can be performed sequentially.

The trapping medium used in the sample cell is translucent, and the light source is disposed to illuminate the trapping medium from inside thereof outwards.

Preferably, the trapping medium has an essentially closed form with a cavity formed inside thereof, with the radiation source being placed inside the cavity. For example, the sample cell may have a substantially spherical shape, and the trapping medium may comprise a concentric layer of the trapping medium.

The radiation source used in the sample cell comprises a light source generating excitation light at the excitation line of the contaminant of interest, and a diffuser for dispersing the excitation light substantially in a $4\pi$ steradian angle.

The sample cell has a fluid inlet communicating with the trapping medium, and a fluid outlet for discharging the aqueous fluid that has passed through the trapping medium.

Additionally, the sample cell may comprise an outer transparent shell, which blocks radiation from the radiation source and passes through the secondary radiation. The outer transparent shell may further incorporate a scintillation material for detecting radioactive elements in the aqueous fluid to be analyzed.

In an alternative implementation of the sample cell, the trapping medium is translucent and has a shape resembling a disk or a slab, having a side surface and respective top and bottom surfaces, the radiation source being disposed to illuminate the trapping medium through the side surface, or alternatively, through at least one of the top surface or bottom surface, causing the contaminant to generate the secondary light through at least one of the top and bottom surfaces.

In the fluid contamination analyzer and the sample cell described above, the trapping medium preferably comprises a three-dimensional matrix of micro-porous adsorbent support material, whose surface has been chemically reconstructed with a surface reconstruction reagent to bear active, hydrated hydroxyl groups, which provide irreversible binding sites, providing absorption and entrapment of colloids and entrained analytes by immobilizing said colloids on said surface through the release of hydronium/hydrogen ions from the hydroxyl groups.

Preferably, the hydroxyl groups are chosen to match the range of contaminant acid constant values, Ka, with an appropriate range of base constant values Kb.

Preferably, said micro-porous support material comprises diatomaceous earth, and the surface reconstruction reagent comprises a metal hydroxide.

A method for analyzing an aqueous fluid containing a contaminant is also provided. It comprises the steps of (a) providing the fluid contamination analyzer as described above; and (b) illuminating the trapping medium with excitation radiation and detecting the secondary radiation at the detector at the same time as the aqueous fluid is flowing through the trapping medium.

BRIEF DESCRIPTION OF THE DRAWINGS

The invention will be described in more detail with the reference to the attached drawings, in which.

DETAILED DESCRIPTION OF PREFERRED EMBODIMENTS

Sample Cell

Figure 1:
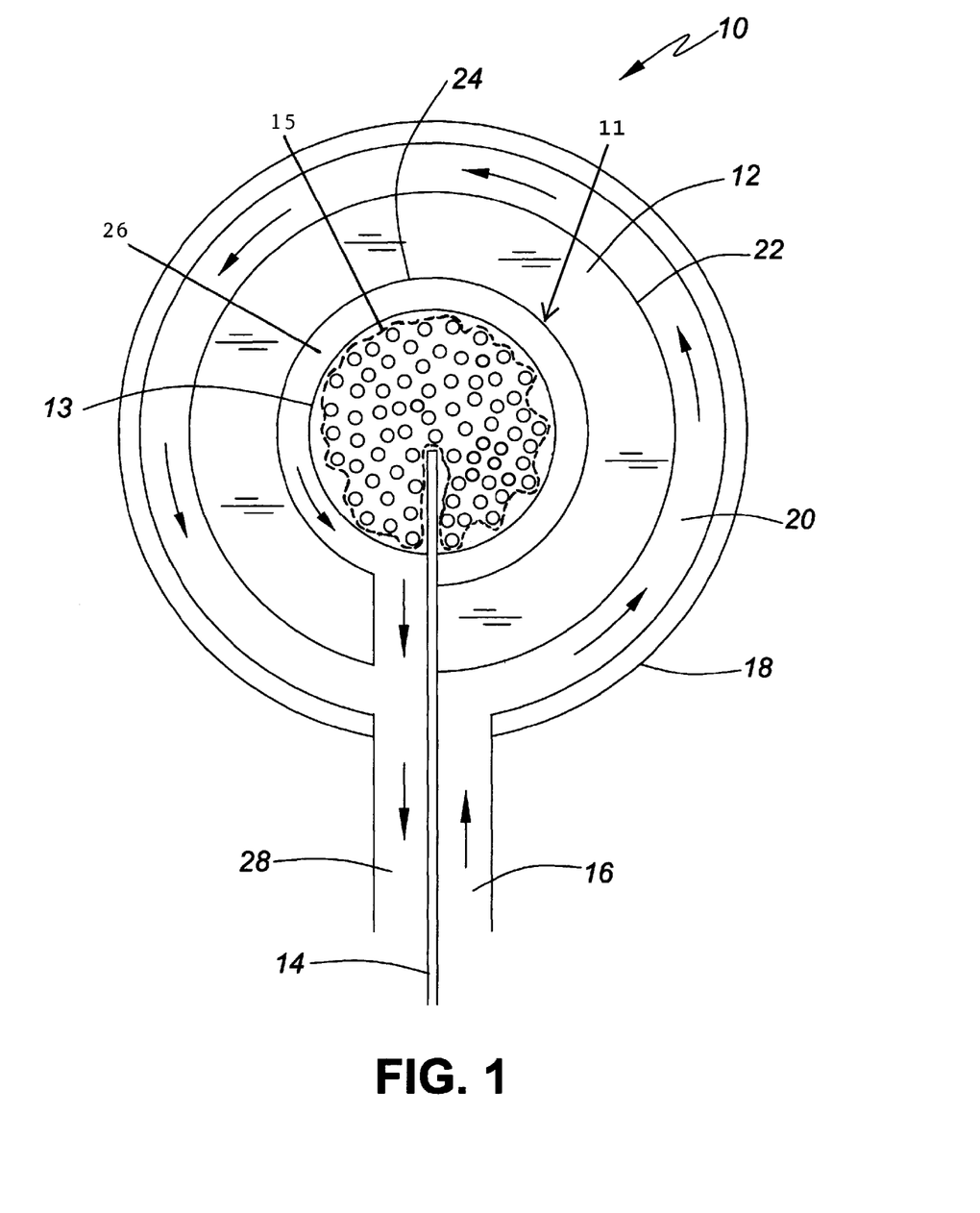
FIG. 1 is a schematic cross-sectional view of one form of a sample cell.
Figure 1A:
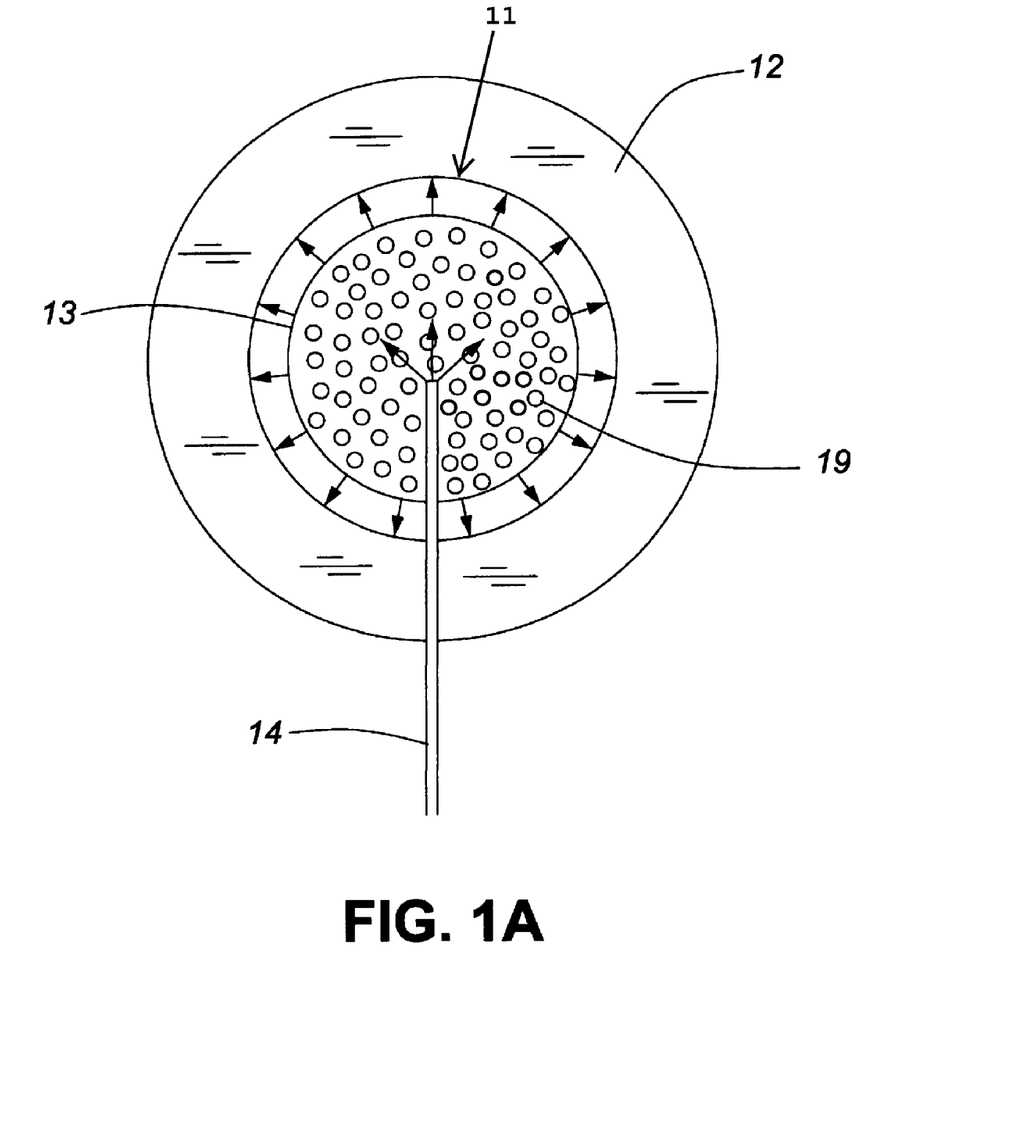
FIG. 1A shows the trapping medium and the radiation source of the sample cell of FIG. 1 in more detail.

FIG. 1 illustrates one form of a sample cell 10 for the fluid contamination analyzer of the embodiment of the present invention, the sample cell 10 being suitable for an optical fluorescent analysis of contaminants. The cell 10 has a substantially spherical shape and includes a concentric layer of the trapping medium 12 for trapping contaminants from a fluid flowing therethrough, the trapping medium having an internal cavity 11, where a radiation source (light source) 13 disposed to illuminate the trapping medium 12 from inside thereof outwards. In the embodiment of the invention, the trapping medium 12 is a gel previously patented by the Applicant and described in detail in the U.S. Pat. No. 5,512,491 to Mehkeri et al. entitled "METHOD FOR ULTRA-TRACE LEVEL ANALYSIS OF WATER" issued Apr. 30, 1996 and Canadian patent No. 2,160,235 to Mehkeri et al entitled "A SYSTEM FOR ULTRA-TRACE LEVEL ANALYSIS OF WATER AND A TRAPPING MEDIUM THEREFOR" issued Jul. 5, 2005. For further clarity, the trapping medium 12 having the internal cavity 11 and the light source 13 of FIG. 1 are also illustrated in FIG. 1A.

For convenience, a short description of the properties of the trapping medium is reproduced below.

The trapping medium may comprise a variety of microporous materials that present "active" hydroxyl groups over the surface of such material. "Active" hydroxyl groups are those capable of forming new bonds with the hydroxyl-bridges found within the colloidal carriers. This is effected through the release or elimination of a hydrogen ion.

Such hydroxyl groups may be formed on the surfaces of both organic and inorganic materials. An inorganic example would be a micro-porous support coated with freshly-prepared aluminum hydroxide. Suitable supports include zeolites, kieselguhr, fuller's or diatomaceous earth, alumina and silica gel. A calcined diatomaceous earth product produced by John Mansville Corporation and sold under the trade mark CELITE® is moderately directly effective in this procedure as it contains active hydroxyl groups in its natural form when hydrated and has a high internal surface area with voids that readily accommodate colloidal material. CELITE®, as with the other referenced micro-porous inorganic materials, will perform in a superior manner if specifically treated to add hydroxyl groups, which are chosen to match the range of contaminant acid constant values, Ka, with an appropriate range of base constant values Kb.

An organic example of a suitable trapping media is the range of porous materials originating from Pharmacia Incorporated of New Jersey and sold under the trade mark SEPHADEX®. This material is a polymerized polysaccharide in the form of beads. Specified pore-sizes can be prepared as required, ranging from 100 to 1 million Daltons. This material contains naturally "active" hydroxyl groups as part of the sugar structure with an appropriate range of Kb values for trapping contaminants.

Trapping media provided with the appropriate range of active hydroxyl groups have the valuable feature that the colloidal carriers become irreversibly bound in the medium. It is believed that this occurs due to a chemical reconstruction process on the surfaces of the medium, in which they become bound by an esterification reaction to the hydroxyl groups. This is suggested by the fact that it has been found that for each ion of the colloid, which is bound, a hydrogen ion is released in its typically hydrated form known as a "hydronium ion". Under electron microscopy, the immobilized colloidal gel can actually be seen accumulated within the pores of the trapping media.

It appears, therefore, that the dissociation constant for the colloidal gels, once absorbed, has been reduced by many orders of magnitude by establishing the conditions of matching Ka and Kb values to achieve complete reaction, called metathesis, compared to trapping on conventional adsorber materials such as AMBERLITE® resins.

The efficiency of the trapping of the heavy metals within trapping media can be influenced, as well, by adjusting the pH of the water sample being fed to the trapping media. The pH may be adjusted to the optimum values for effecting the precipitation, as hydroxides, of the metal, or groups of metals being isolated.

Such metathetical trapping media make possible the ultra-trace analysis of contaminants of greatest concern to society, e.g. the detection of hydrophobic organic substances and insoluble hydroxides of heavy metals. Examples include polychlorinated biphenyls (PCB's), dioxins, furans, polycyclic aromatic hydrocarbons (PAH's), lead, chromium, cadmium, mercury, etc. The metathetical trapping media may also be capable to accumulate and concentrate bacterial, protozoa, diatoms and other microbiota.

Referring back to FIGS. 1 and 1A, the light source 13 is formed within the internal cavity 11 of the trapping medium 12. The light source 13 has a diffuser 15, comprising a plurality of dispersing elements 19, e.g. in the form of small glass or plastic balls (beads) or similar objects, which scatter light in various directions, and an optical fiber 14 supplying the excitation light at the excitation line of the fluorescence for the analyte of interest to illuminate the dispersion elements 19. The optical fiber 14 illuminates the diffuser 15 approximately at the centre thereof, causing the dispersion elements 19 to scatter the excitation light in substantially $4\pi$ steradian and illuminate the trapping medium 12 substantially isotropically.

Other components of the sample cell 10 are as follows:

A water feed in passage 16 for supplying water to the sample cell 10, which is facilitated by a inlet tube or capillary connected to a pump;

An outer transparent shell 18, which is made of a transparent plastic or similar material, and serves as a suitable emission band pass optical filter for the excitation light;

An input water channel 20 in the form of a concentric passage, which conducts the water symmetrically around the trapping medium 12;

An outer porous surface 22, which is adjacent to or deposited on the outer surface of the trapping medium 12 and provides structural support against the influx of water from the input water channel 20 to prevent the trapping medium 12 from being washed away;

An inner perforated membrane 24, such as aluminized Mylar®, which is adjacent to or deposited on the inner surface of the trapping medium 12 and provides structural support for the trapping medium 12 so as to prevent wash through and maintain the position of the trapped trace contaminants. Preferably, the inner perforated membrane 24 is also reflective to the fluorescence line of the secondary light emitted by the contaminants entrapped in the trapping medium 12;

An output water channel 26 in the form of a concentric passage between the trapping medium 12 and the light source 13, which conducts the water symmetrically around the light source 13 and outside of the sample cell 10; and A water feed output passage 28 for removing water from the sample cell 10, which is facilitated through the holes in the inner perforated membrane 24 past the diffuser 15 and out through an outlet tube or capillary. Conveniently, the outlet pipe may also serve to deliver the optical fiber 14 to illuminate the diffuser 15.

In operation, the contaminated water or any other aqueous fluid to be analyzed is passed through the sample cell 10 via an inlet tube 16 and then through the trapping medium 12, which collects contaminants present in the water flowing therethrough. The water is withdrawn through an outlet tube 28. The light source 13 provides substantially isotropic illumination of the trapping medium 12 from inside outwards. When the trapping medium is illuminated by the light source 13, the contaminants entrapped in the trapping medium 12 emit secondary fluorescent light (secondary radiation), which is collected and analyzed in the fluid contamination analyzer of the embodiment of the present invention as will be described in detail below.

The water path in the sample cell 10 is as follows. The water containing the analyte of interest is pumped into the sample cell via an inlet tube or capillary 16 where it travels into the input water channel 20. Then the water travels through the outer porous surface 22 and through the trapping medium 12. The water flow then continues through the inner perforated membrane 24 to the water output channel 26 past the light source 13, and then out of the sample cell 10 through the water feed output 28.

The light path in the sample cell 10 is as follows. The excitation light is guided from a source (not shown), e.g. a laser, through the optical fiber 14 into the diffuser 15. The optical fiber 14 may be separate or conveniently contained in the water feed output 28. The excitation light is scattered by the dispersion elements 19 within the diffuser 15 and then propagates through the inner perforated membrane 24 and illuminates the analyte of interest within the trapping medium 12. The optically excited analyte then emits secondary (fluorescent) light sending it substantially in all directions. Part of this secondary fluorescent light propagates through the trapping medium 12, the water input channel 20, the outer porous surface 22, and further through the outer transparent surface 18. To facilitate propagation of the other part of the secondary fluorescent light, a reflective coating is preferably placed on the surfaces of the inner perforated membrane 24, the outer transparent surface 18 and possibly on the outer porous surface 22 should the need arise.

In general, the sample cell 10 described above satisfies the following requirements:

the trapping medium has an essentially closed form with a cavity inside the trapping medium, e.g. the trapping medium 12 may have a form of a spherical layer as described above;

the trapping medium is illuminated from inside thereof and outwards, e.g. the trapping medium is illuminated from inside the cavity 11 by the light source 13 as described above;

an excitation light source is used to excite fluorescent molecules entrapped in the trapping medium;

an optical filtering mechanism is used to filter excitation photons while being transparent to the fluorescent photons emitted from the entrapped contaminants;

the water flow around the trapping medium has to remain low enough in turbidity in order to prevent the clogging of the porous surfaces and not to obstruct light propagation;

the trapping medium is made sufficiently translucent by the surface activation reaction to allow sufficient propagation of the excitation light inside the volume to cause the excitation of the entrapped contaminants.

The spherical structure of the sample cell 10 should be amenable to disassembling for loading and removal of the trapping medium 12, the dispersing elements 19 and the optical fiber 14. To this end, the sample cell 10 may be constructed of two halves, with their division plane approximately coextensive with, or parallel to the axis of the optical fiber 14. The two halves may be assembled using waterproof seals. Alternatively, the sample cell 10 may be constructed of a number of symmetrical or asymmetrical sectors instead of the two halves, which can be removed separately, and when assembled, would form the sample cell 10 of FIG. 1.

The overall structure of the sample cell 10 has preferred dimensions in the range of a few centimeters in diameter, e.g. about 2 cm diameter. Larger dimensions of the sample cell 10 are also possible, e.g. in the range of a few decimeters or larger, provided the sample cell is to be used in a stationary fluid contamination analyzer, which does not have to be portable. In this case, the weight and dimensions of the sample cell 10 and fluid contamination analyzer are not of utmost importance.

The sample cell 10 may also be altered to incorporate a scintillating material in the outer transparent shell 18. This would allow for the detection of radioactive elements in fluids by observing the radiation emitted through an interaction with the radiation produced by the decay of the analyte and the scintillator.

Another form of Sample Cell

Figure 2:
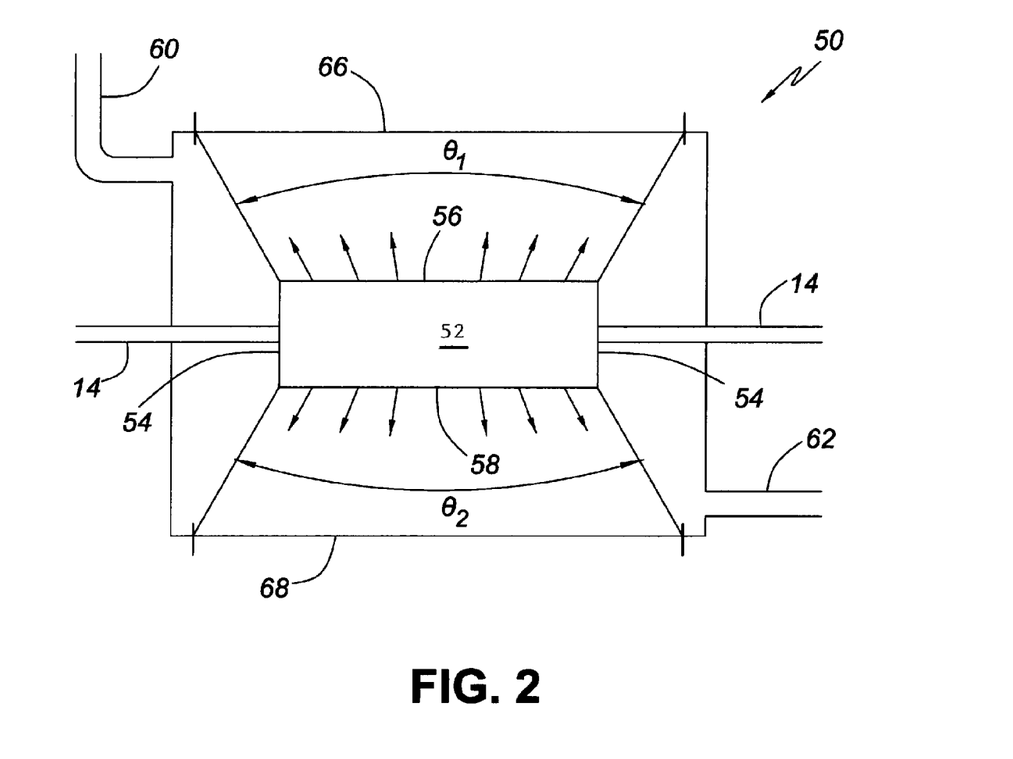
FIG. 2 is a schematic cross-sectional view of another form of the sample cell.

FIG. 2 illustrates another form of the sample cell 50 for the fluid contamination analyzer of the embodiment of the present invention. The sample cell 50 has a substantially planar geometry and holds a disk-shaped trapping medium 52 (mounting means are omitted for simplicity), having a side surface 54 and top and bottom surfaces 56 and 58 respectively. A fluid is supplied into the sample cell 50 through a fluid inlet 60, enters the trapping medium 12 through its top surface 56, flows through the trapping medium 52, and exits the trapping medium through its bottom surface 58, being removed from the sample cell 50 via fluid outlet 62. The light source is implemented in the form of at least one or more optical fibers 14, which illuminate the side surface 54 of the trapping medium 52 with the excitation light, the optical fibers being arranged preferably symmetrically so as to illuminate the side surface 54 substantially uniformly. The secondary fluorescent radiation indicative of the presence and concentration of fluid contaminants present in the fluid is stimulated by the excitation light and radiated through the top and bottom surfaces 56 and 58 of the trapping medium 52, and through respective top and bottom windows 66 and 68 of the sample cell 50. Thus, in the sample cell 50, the secondary fluorescent radiation is emitted substantially into a $2\pi$ steradian angle $\theta_1$ through the top surface 56 of the trapping medium 50, and substantially into a complementary $2\pi$ steradian angle $\theta_2$ through the bottom surface 58 of the trapping medium 50.

It is contemplated that various modifications are possible to the design of the sample cell 50. The sample cell 50 may comprise more than one disk-shaped trapping medium 52, the trapping medium 52 itself may have a different shape, e.g. slab like or other, the orientation of the trapping medium 52 within the sample cell and the respective fluid flow through the trapping medium 12 may be changed, e.g. the trapping medium 52 may be rotated at an angle, e.g. at approximately 90 degrees, compared to its current position shown in FIG. 2. Illumination of the trapping medium 52 may be performed differently, e.g. the primary radiation may illuminate one of the top or bottom surfaces 56 or 58 of the medium 52, or, alternatively, both top and bottom surfaces 56 and 58. The form of the light source may be also different as long as it supplies sufficient energy to illuminate the trapping medium 52 at the excitation line of the analyte of interest to generate enough secondary fluorescent radiation for detection purposes.

Thus, improved sample cells 10 and 50 for fluid contamination analysis have been provided.

Fluid Contamination Analyzer

Figure 3:
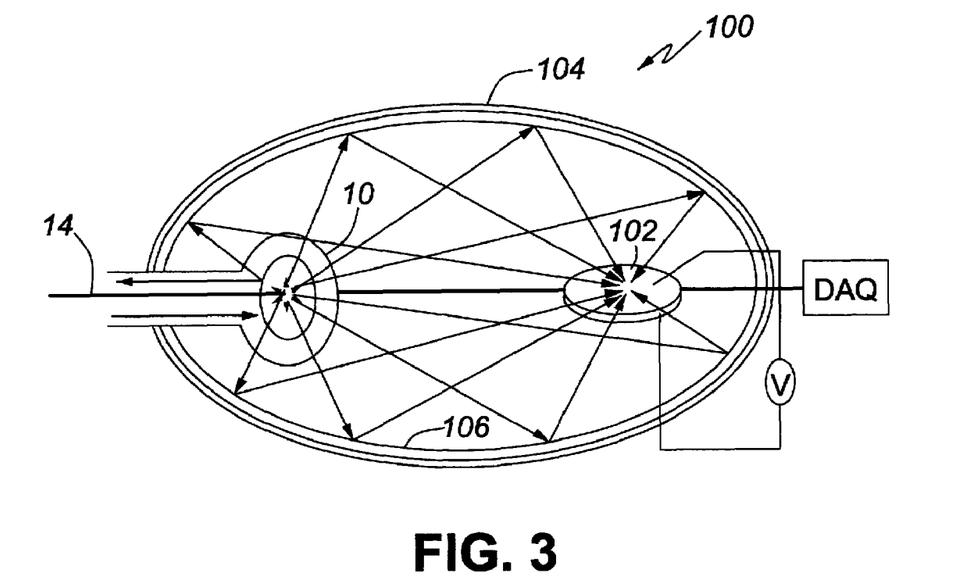
FIG. 3 shows a schematic cross-sectional view of an exemplary fluid contamination analyzer according to the embodiment of the invention.

FIG. 3 illustrates the fluid contamination analyzer 100 of the embodiment of the present invention. The fluid contamination analyzer 100 comprises the sample cell 10 described above, a detector 102 for detecting the secondary radiation; and a reflective shell 104 in the form of an ellipsoid, at least partly encompassing the sample cell 10 and the detector 102, the reflective shell 104 defining two focal points so that radiation generated at one of the focal points is reflected by the reflective shell to the other focal point, wherein the sample cell 10 is disposed at or in close proximity to one of the focal points, and the detector 102 is disposed at or in close proximity to the other focal point to receive the secondary fluorescent radiation generated by the entrapped contaminant. The reflective shell 104 is preferably made of aluminum metal and has an internal reflective surface 106 made of gold or another suitable reflective material.

The shape of the reflective shell can be different, for example, non-continuous in the form, e.g. of a truncated ellipsoid, or resembling a hyperboloid or paraboloid as long as it serves the purpose of focusing the secondary fluorescent light emitted from the sample cell 10 onto the detector 102, which is spaced from the sample cell 10.

Figure 4:
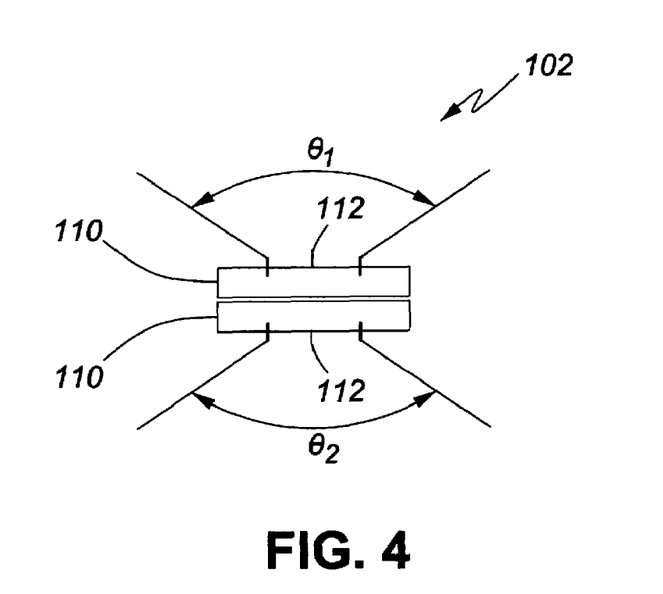
FIG. 4 illustrates one form of a detector for use in the fluid contamination analyzer of FIG. 3.

One form of the detector 102 is illustrated in FIG. 4. It comprises two back-to-back silicon photo avalanche diodes 110, with their detecting windows 112 facing in opposite directions and capable of collecting light from substantially complementary $2\pi$ steradian angles $\theta_1$ and $\theta_2$ as illustrated in FIG. 4. Accordingly this form of the detector 102 will be referred to as a "$2\pi$ detector".

Another form of the detector 102 includes an optimized solid state device as its detecting component, which has a spherical shape and is preferably made of silicon. It is operated via radio frequency or hard wired to the detector. Currently, a prototype for such solid state device is available from Ball Semiconductor Inc. of Allen, Tex., USA, which manufacturers small spherical chips of about 1 mm in size.

Preferred Requirements for the Fluid Contamination Analyzer 100:

(1) The dimensions for the reflective shell are preferably of the order of 1 foot to 2 foot length by one foot in diameter (or smaller). These dimensions will be optimized for light capturing efficiency depending on the dimensions of the sample cell 10 and the detector 102, however they illustrate that the fluid contamination analyzer is intended to be portable;

(2) As mentioned previously, the turbidity of the fluid in the sample cell 10 should be kept low enough to prevent fouling of the flow apparatus. This will be characterized by the size of the porous surfaces and flow rate;

(3) There is also a possible requirement of in an inert atmosphere, e.g. nitrogen as certain flat chip detectors may have to be operated in such an environment due to manufacturer's specifications. This may also help hinder the growth of oxides on the coatings found on the optics or internal reflective surface 106. If this is necessary, then vacuum seals will be employed anywhere there are joints to the outside;

(4) As discussed above, the trapping medium 12 is to be disposable and hence removable so as to make the sample cell 10 or 50 reusable; and (5) The detector, 102, itself may require an anti-reflection (AR) coating to limit the reflection of grazing angle radiation.

As already mentioned, the contaminants are usually present in water, or any other aqueous fluid, in trace amounts. Therefore, in order to accumulate the amount of the contaminant in the trapping medium 12, which would be sufficient to provide a reliable reading at the detector 102, it is understood that the volume of water may have to be passed through the cell for a required period of time.

The fluid contamination analyzer 10 can function in two modes of operation.

In a sequential mode of operation, the fluid to be analyzed is passed through the trapping medium for a predetermined period of time to allow the accumulation of the sufficient amount of the contaminant, and after that the secondary light fluorescent analysis of the entrapped contaminant is performed in the manner described above.

In a parallel mode of operation, the light source 13 is illuminating the trapping medium, and the detector 102 is detecting the secondary fluorescent light at the same time as the fluid is flowing through the trapping medium 12. This allows monitoring of the dynamics of accumulation of the contaminant in the trapping medium and, in certain occasions, to reduce the time required for the contamination analysis, e.g. when only the presence of the contaminant has to be detected.

It is understood that, in the fluid contamination analyzer 100, the sample cell 50 described above can be also used instead of the sample cell 10. Other designs of sample cells are also possible as long as they provide a dual function of entrapping contaminants present in the fluid to be analyzed, and analyzing the presence and concentration thereof by using optical methods.

Although a fluorescence optical analysis of contaminants has been used in the preferred embodiment of the invention, it is contemplated that other spectroscopic techniques, which generate the measurable presence or absence of the secondary light indicative of the identity and concentration of contaminants, can be also employed within the spirit of the present invention.

The fluid contamination analyzer 100 of the embodiment of the present invention has the following advantages.

The fluid contamination analyzer 100 would not only provide a device that is small, rugged, field-portable and in-situ tool, but will also provide an improved detection sensitivity by a minimum of two orders of magnitude compared to currently commercial available analyzers. It is suitable for environmental analysis of micro-organisms, organic and inorganic substances found in various fluids, e.g. freshwater sources.

Furthermore, the fluid contamination analyzer 100 allows a simplified installation and removal of the trapping medium 12, which enables users to conduct sampling more frequently. This will empower plant managers with the ability to manage water in a real time, i.e. in a prevention mode as opposed to the historical monitoring and remediation mode used currently.

Thus, although particular embodiments of the invention have been described in detail, it can be appreciated that alternatives, such as those mentioned above and numerous other changes, variations, and adaptations may be made without departing from the scope of the invention as defined in the following claims.

What is claimed is:

1. A fluid contamination analyzer comprising:
   (a) a sample cell, comprising:
      (i) a trapping medium for entrapping a contaminant from an aqueous fluid flowing through the trapping medium, the trapping medium having an outer surface and an inner surface;
      (ii) the trapping medium is translucent and has an essentially closed form defined by the outer surface, with a cavity formed inside thereof defined by the inner surface;
      (iii) an outer structural support surface and an inner structural support surface formed on or adjacent to the outer surface and the inner surface respectively; and
      (iv) a radiation source illuminating the trapping medium with excitation radiation to cause the entrapped contaminant to generate a secondary radiation indicative of an identity of the entrapped contaminant, or the identity and concentration of the entrapped contaminant; the radiation source is placed inside the cavity to illuminate the trapping medium from inside thereof outwards;
   (b) a detector for detecting the secondary radiation; and
   (c) a reflective shell at least partly encompassing the sample cell and the detector, the shell having a shape defining two focal points so that radiation generated at one of the focal points is substantially reflected by the reflective shell to the other focal point, the sample cell being disposed at or in close proximity to one of the focal points, and the detector being disposed at or in close proximity to the other focal point to receive the secondary radiation generated by the entrapped contaminant.

2. The fluid contamination analyzer according to claim 1, wherein the radiation source is illuminating the trapping medium and the detector is detecting the secondary radiation at the same time as the fluid is flowing through the trapping medium.

3. The fluid contamination analyzer according to claim 1, wherein the reflective shell has an ellipsoidal shape.

4. The fluid contamination analyzer according to claim 1, wherein the reflected shell has a shape of a truncated ellipsoid.

5. The fluid contamination analyzer according to claim 1, wherein the reflective shell has one of the following shapes:
   a hyperboloid;
   a truncated hyperboloid;
   a paraboloid;
   a truncated paraboloid.

6. The fluid contamination analyzer according to claim 1, wherein the secondary radiation is a fluorescent radiation generated by the entrapped contaminant.

7. The fluid contamination analyzer according to claim 1, wherein the secondary radiation or lack thereof is generated in one of the following spectroscopic techniques: Magnetic Circular Dichroism (MCD); Scattering, comprising Raman scattering; Scintillation; Photo-Acoustic; Fluorescence; Phosphorescence; Luminescence; or Absorbance.

8. The fluid contamination analyzer according to claim 1, wherein the detector comprises two back-to-back photo-detectors, having their detecting windows facing in substantially opposite directions.

9. The fluid contamination analyzer according to claim 1, wherein the detector comprises a semiconductor ball, which is used as a detecting component in the detector.

10. The fluid contamination analyzer according to claim 1, wherein the sample cell has a substantially spherical shape, and the trapping medium comprises a concentric layer of the trapping medium.

11. The fluid contamination analyzer according to claim 1, wherein the radiation source comprises a diffuser for dispersing the excitation radiation substantially in a $4\pi$ steradian angle.

12. The fluid contamination analyzer according to claim 1, wherein the sample cell has a fluid inlet communicating with the trapping medium, and a fluid outlet for discharging the fluid that has passed through the trapping medium.

13. The fluid contamination analyzer according to claim 1, wherein the sample cell comprises an outer transparent shell, which blocks the excitation radiation and passes through the secondary radiation.

14. The fluid contamination analyzer according to claim 13, wherein the outer transparent shell further incorporates a scintillation material for detecting radioactive elements in the aqueous fluid.

15. A sample cell, comprising:
   (i) trapping medium for entrapping a contaminant from an aqueous fluid flowing through the trapping medium, the trapping medium having an outer surface and an inner surface;
   (ii) the trapping medium is translucent and has an essentially closed form defined by the outer surface, with a cavity formed inside thereof defined by the inner surface;
   (iii) an outer structural support surface and an inner structural support surface formed on or adjacent to the outer surface and the inner surface respectively; and
   (iv) a radiation source illuminating the trapping medium with excitation radiation to cause the entrapped contaminant to generate a secondary radiation indicative of an identity of the contaminant, or the identity and concentration of the contaminant; the radiation source is placed inside the cavity to illuminate the trapping medium from inside thereof outwards.

16. The sample cell according to claim 15, wherein the radiation source is illuminating the trapping medium at the same time as the aqueous fluid is flowing through the trapping medium.

17. The sample cell according to claim 15, wherein the sample cell has a substantially spherical shape, and the trapping medium comprises a concentric layer of the trapping medium.

18. The sample cell according to claim 15, wherein the radiation source comprises a diffuser for dispersing the excitation radiation substantially in a $4\pi$ steradian angle.

19. The sample cell according to claim 15, wherein the sample cell has a fluid inlet communicating with the trapping medium, and a fluid outlet for discharging the aqueous fluid that has passed through the trapping medium.

20. The sample cell according to claim 15, comprising an outer transparent shell, which blocks the excitation radiation and passes through the secondary radiation.

21. The sample cell according to claim 20, wherein the outer transparent shell further incorporates a scintillation material for detecting radioactive elements in the aqueous fluid.

22. The fluid contamination analyzer according to claim 1, wherein the trapping medium comprises a three-dimensional matrix of micro-porous adsorbent support material, whose surface has been chemically reconstructed with a surface reconstruction reagent to bear active, hydrated hydroxyl groups, which provide irreversible binding sites, providing absorption and entrapment of colloids and entrained analytes by immobilizing said colloids on said surface through the release of hydronium/hydrogen ions from the hydroxyl groups.

23. The fluid contamination analyzer according to claim 22, wherein the hydroxyl groups are chosen to match a range of contaminant acid constant values, Ka, with an appropriate range of base constant values Kb.

24. The fluid contamination analyzer according to claim 22, wherein said micro-porous support material comprises diatomaceous earth.

25. The fluid contamination analyzer according to claim 22, wherein the surface reconstruction reagent comprises a metal hydroxide.

26. The sample cell according to claim 15, wherein the trapping medium comprises a three-dimensional matrix of micro-porous adsorbent support material, whose surface has been chemically reconstructed with a surface reconstruction reagent to bear active, hydrated hydroxyl groups, which provide irreversible binding sites, providing absorption and entrapment of colloids and entrained analytes by immobilizing said colloids on said surface through the release of hydronium/hydrogen ions from the hydroxyl groups.

27. The sample cell according to claim 26, wherein the hydroxyl groups are chosen to match a range of contaminant acid constant values, Ka, with an appropriate range of base constant values Kb.

28. The sample cell according to claim 26, wherein said micro-porous support material comprises diatomaceous earth.

29. The sample cell according to claim 26, wherein the reconstruction reagent comprises a metal hydroxide.

30. A method for analyzing a fluid containing a contaminant, comprising the steps of:
   (a) providing the fluid contamination analyzer according to claim 1; and
   (b) illuminating the trapping medium with excitation radiation and detecting the secondary radiation at the detector at the same time as the aqueous fluid is flowing through the trapping medium.

31. The sample cell according to claim 15, comprising an inner transparent shell disposed in the cavity and substantially surrounding the radiation source, which blocks the secondary radiation and passes through the excitation radiation.

32. The fluid contamination analyzer according to claim 1, where the sample cell comprises an inner transparent shell disposed in the cavity and substantially surrounding the radiation source, which blocks the secondary radiation and passes through the excitation radiation.

33. The sample cell according to claim 15, further comprising a fluid feed in passage for supplying the aqueous fluid to the sample cell, and a fluid feed output passage for discharging the aqueous fluid that has flowed through the trapping medium from the sample cell, the fluid feed output passage being formed inside the cavity.

34. A fluid contamination analyzer according to claim 1, the sample cell further comprising a fluid feed in passage for supplying the aqueous fluid to the sample cell, and a fluid feed output passage for discharging the aqueous fluid that has flowed through the trapping medium from the sample cell, the fluid feed output passage being formed inside the cavity.

* * * * *